(12) United States Patent
Prey (10) Patent No.: US 10,294,606 B2
(45) Date of Patent: May 21, 2019

(54) METHOD AND SYSTEM FOR MAINTAINING AT LEAST ONE PROTECTIVE SUIT

(71) Applicant: RUD. PREY GmbH & Co. KG, Kiel (DE)

(72) Inventor: Thomas Prey, Kiel (DE)

(73) Assignee: Rud. Prey GmbH & Co. KG, Kiel (DE)

( * ) Notice: Subject to any disclaimer, the term of this patent is extended or adjusted under 35 U.S.C. 154(b) by 16 days.

(21) Appl. No.: 15/172,394

(22) Filed: Jun. 3, 2016

(65) Prior Publication Data

US 2016/0355973 A1    Dec. 8, 2016

(30) Foreign Application Priority Data

Jun. 3, 2015    (DE) .................... 10 2015 108 857

(51) Int. Cl.
| | |
|---|---|
| D06F 59/02 | (2006.01) |
| A61L 2/18 | (2006.01) |
| B08B 9/00 | (2006.01) |
| F26B 21/00 | (2006.01) |
| G01M 3/02 | (2006.01) |
| B08B 13/00 | (2006.01) |
| G01M 3/26 | (2006.01) |
| A62B 17/00 | (2006.01) |

(52) U.S. Cl.
CPC ............ *D06F 59/02* (2013.01); *A61L 2/18* (2013.01); *B08B 9/00* (2013.01); *B08B 13/00* (2013.01); *F26B 21/008* (2013.01); *G01M 3/027* (2013.01); *G01M 3/26* (2013.01); *A61L 2202/17* (2013.01); *A61L 2202/26* (2013.01); *A62B 17/006* (2013.01); *B08B 2209/085* (2013.01)

(58) Field of Classification Search
None
See application file for complete search history.

(56) References Cited

U.S. PATENT DOCUMENTS 6,516,536 B2    2/2003    Ryden
2001/0049883 A1 *  12/2001   Ryden

FOREIGN PATENT DOCUMENTS

WO    WO2007/003191 A *    1/2007

* cited by examiner

*Primary Examiner* — Michael E Barr
*Assistant Examiner* — Jason P Riggleman
(74) *Attorney, Agent, or Firm* — Barclay Damon LLP (57) ABSTRACT

A method for maintaining at least one protective suit. The method comprises connecting at least one maintenance adapter in a detachable and sealing manner to at least one aperture of the protective suit. Cleaning and disinfecting is passed through the maintenance adapter and into the inside of the protective suit and is subsequently discharged. Drying gas is then passed through the maintenance adapter into the inside of the protective suit and subsequently discharged.

16 Claims, 4 Drawing Sheets

METHOD AND SYSTEM FOR MAINTAINING AT LEAST ONE PROTECTIVE SUIT

CROSS REFERENCE TO RELATED APPLICATION

This application is based upon and claims priority to German Patent Application No. 10 2015 108 857.6, filed Jun. 3, 2015, under relevant sections of 35 USC § 119, the entire contents of which are hereby incorporated by reference.

BACKGROUND OF THE INVENTION

The invention relates to a method and system for maintaining at least one Protective Suit, especially a Chemical Protection Suit. Chemical Protection Suits (CPS) are part of the Personal Protective Equipment (PPE) of firefighters and other rescue teams. They protect the user against external influences and allow for temporary work in areas contaminated by chemicals. By using a Chemical Protection Suit, exposure to harmful substances and gases through the skin and body cavities is prevented. Chemical Protection Suits are divided into different types (according to DIN 943-1, 943-2, 14605, 13982-1, 13034):

Type 1—"Gas-tight" Chemical Protection Suit [DIN 943-1 and 943-2].

A Type 1a-ET Gas-tight Chemical Protection Suit is for use by emergency teams with an ambient-air-independent breathing air supply worn inside the Chemical Protection Suit, for example, a container unit with compressed air (SCBA or Self-Contained Breathing Apparatus).

A Type 1b-ET Gas-tight Chemical Protection Suit for use by emergency teams with a breathing air supply worn outside of the Chemical Protection Suit, for example, a container unit with compressed air (SCBA or Self-Contained Breathing Apparatus).

Type 1c—"Gas-tight" Chemical Protection Suit with breathing air supply with overpressure, for example, from external lines.

Type 2—"Non-gas-tight" Chemical Protection Suit [DIN 943-1] with a breathing air supply with overpressure.

Type 3—"Liquid-tight" Chemical Protection Suit [DIN 14605].

Type 4—"Spray-tight" Chemical Protection Suit [DIN 14605].

Type 5—"Airborne-particle-tight" Chemical Protection Suit [DIN 13982-1].

Type 6—"Limited liquid chemicals" Chemical Protection Suit [DIN 13034].

For Chemical Protection Suits of types 1 and 2, a distinction is made between suits for a limited use (disposable) and the reusable insert. Following current regulations, only Chemical Protection Suits of type 1a and 1b ET-ET are approved for use (ET: Emergency Team) as personal protection equipment for firefighters. The present invention is concerned preferably with reusable Chemical Protection Suits of types 1a and 1b ET-ET.

BRIEF SUMMARY OF THE INVENTION

A method for maintaining at least one protective suit, especially a Chemical Protection Suit, comprising the steps of: a) at least one maintenance adapter with a detachable and sealing connection to at least one aperture of the protective suit; b) a cleaning and disinfecting fluid is directed via at least one maintenance adapter into the inside of the suit and the led into the inside of the suit cleaning and disinfection fluid is discharged out of the protective suit; c) a drying gas for drying the protective suit is directed via at least one maintenance adapter into the inside of the protective suit and the guided into the inside of the suit drying gas is discharged out of the protective suit, at least one maintenance adapter is separated from the at least one aperture of the suit.

The invention also relates to a corresponding system.

BRIEF DESCRIPTION OF THE DRAWINGS

An embodiment of the invention is explained in more detail with reference to figures. Schematically.

DETAILED DESCRIPTION OF THE INVENTION

Reusable Chemical Protection Suits must be maintained. The care may include regular cleaning, disinfection, and drying of the Chemical Protection Suit inside and out, as well as a visual inspection for damage, and a leak test of the suit and the exhaust device (exhaust device and exhaust valve outlet(s)). Additional steps in the maintenance protocol may include the greasing of the zipper which forms the access for the user and applying a defogging solution to the visor. The enumerated maintenance work must be carried out after each use or any exercise in which the CPS is used. The leak test and exhaust valve test need to be carried out in vendor-specific intervals, even if the suit has not been used twice a year up to at least three years. Contaminated, soiled or polluted Chemical Protection Suits must be first decontaminated on site (removal of hazardous pollution) as well as packaged and labeled (use, location, type of contamination) airtight in special containers (for example, overpacks or contamination bags). Highly contaminated suits that were contaminated with toxic water insoluble substances must be phased out and disposed of properly.

The maintenance work must be performed in a specially equipped respiratory protection workshop. Before maintenance, Chemical Protection Suits must be checked for any residual contamination.

The serviceman or other trained personnel must wear a CPS in order to carry out maintenance work of the CPS light protection equipment. Besides chemical contaminants, other pollutants can stick to the outer layer of the CPS such as oils sands, biological waste, and other liquids and solids. The impurities inside the suits may consist of contamination by germs caused by sweat, exhaled air, dander, and hair of the user.

In the context of exercises, exercise suits or (discarded) previously used suits may be used. Here, however, contamination with hazardous substances must be excluded in order to perform maintenance without further precautions.

Chemical Protection Suits must be cleaned according to the manufacturer or the service manuals. An example is, the outside of the Chemical Protection Suit is first cleaned manually with the aid of soft sponges or brushes and a mild-duty detergent. After the suit has been rinsed with clean water, the internal cleaning can be carried out. Another example of cleaning is the cleaning is done in an industrial washing machine.

In contrast to the above two processes, some CPS Maintenance Systems allow simultaneous cleaning of multiple Chemical Protection Suits. If such cleaning of multiple Chemical Protection Suits takes place in an industrial washing machine, the cleaning program is to be selected according to the manufacturer specifications. The industrial washing machine is quite close to a household washing machine; however, it is dimensioned substantially larger. It allows in one cycle only the cleaning and disinfection of one Chemical Protection Suit. By using additional accessories, respirators can be cleaned and disinfected.

After cleaning, the protective suits are rinsed and disinfected. The choice of using disinfectant is defined in the manufacturer specifications. With manual disinfection, the disinfectant can be applied internally and externally by means of a spray lance. In industrial washing machines and CPS Maintenance Systems, the disinfection can be carried out using a heavy-duty detergent disinfectant.

The drying of the CPS may vary depending on the manufacturer and type of air drying, drying in an oven or must be carried out using a drying system at temperatures up to 50° C. (manufacturer's instructions must be respected). It should be ensured that the CPS are not exposed to direct sun or heat radiation. This is intended to avoid damage to the material the CPS is made from.

After an initial visual inspection for defects, the leak and exhaust valve tests are performed. The examination for gas tightness of a Chemical Protection Suit must be carried out in accordance with BGG/GUV-G 9102 at least once per year and after each use, or exercise. The test method determines the tightness of the Chemical Protection Suit from the inside to the outside, although the risk of leakage in the practical application is generally from outside to inside. It is however recommended to periodically check that the tightness from the inside to the outside is equal to the tightness from the outside to the inside. The leak test is performed at a test aperture defined by the manufacturer (exhaust system, exhalation valve, and test connection) and is carried out in accordance with DIN EN 464 or according to manufacturer's instructions.

For maintenance of Chemical Protection Suits, open and closed care systems are known. With an open maintenance system, a multifunctional rack is provided, on which the Chemical Protection Suit that is in need of maintenance is spread. The multifunctional rack comprises several lances or the like to be introduced among others into the leg and arm openings of the Chemical Protection Suit. The lances include cleaning agent (media) outlets which may be used for a detergent or other cleaning or disinfecting agent. Fluid-handling equipment, such as pumps, fans, heating systems, and program control, are stored in a decentralized (remote) control unit. In an embodiment, the various media, such as cleaning and disinfecting solutions as well as drying air, are introduced via hose connection from the decentralized control unit through the partly opened zipper of the Chemical Protection Suit on the multifunctional rack. The Chemical Protection Suit is upside down on the multifunctional rack and the cleaning agents (media) are introduced through the partially opened zipper of the Chemical Protection Suit and they are discharged after their distribution in the suit back through the partially opened zipper, wherein air escapes automatically through the zipper and liquids are pumped. In this way multiple Chemical Protection Suits may be cleaned, disinfected, and dried from the inside.

In contrast, a manual cleaning and disinfection of the suits must be done from the outside.

Closed maintenance systems used for the inside maintenance process of Chemical Protection Suit follow the same procedure as described above for the open maintenance system. However, closed maintenance systems have a splash-proof maintenance cabin in which—in addition—via appropriately positioned nozzles an exterior cleaning, disinfection, and drying of the Chemical Protection Suit is carried out.

The known maintenance systems thus enable a semi-automated cleaning, disinfection, rinsing, and drying of Chemical Protection Suits. However, the known systems require maintenance in addition of a considerable manual effort. In particular, the alignment of the to be maintained Chemical Protection Suits on the multifunctional rack is time consuming and physically demanding. In addition, an automated leak test is not possible because the required pressure buildup inside the to be maintained Chemical Protection Suit that has a partially opened zipper cannot take place. Therefore, in the known maintenance systems, manual maintenance leak tests must be carried out by the serviceman. The corresponding inside pressure test is stipulated under DIN EN 464. This results in a significant time requirement and physical demand from the serviceman.

Accordingly, the invention has therefore the object to provide a method and a system for the maintenance of at least one protective suit, with which the maintenance of protective suits can be done faster and with less effort.

In one embodiment, a method for maintaining at least one protective suit, especially a Chemical Protection Suit, may comprise the steps of: at least one maintenance adapter is connected to at least one aperture of the protective suit in a detachable and sealing fashion; via this at least one maintenance adapter, a cleaning and disinfecting fluid is directed into the inside of the protective suit and is subsequently discharged out of the protective suit; via this at least one maintenance adapter, a drying gas for drying the protective suit is directed into the inside of the protective suit and is then discharged out of the protective suit. The at least one maintenance adapter is at the end separated from the at least one aperture of the protective suit.

In an embodiment, the system for maintaining at least one protective suit, especially a Chemical Protection Suit, comprises at least one maintenance adapter that is connected to at least one aperture of the protective suit in a detachable and sealing fashion. In addition, the system may include a cleaning and disinfecting fluid supply system connectable with the at least one maintenance adapter for introducing a cleaning and disinfecting fluid into the inside of the suit and for discharging said fluid from the protective suit. A connectable drying gas supply system may be included for introducing a drying gas into the inside of the suit and for discharging said gas from the protective suit. In an embodiment, the entire maintenance process may be coordinated or controlled by a controller.

In another embodiment, at least one maintenance adapter is connected with at least one aperture of the suit by at least one detachable and sealing connection. The cleaning, disinfecting and drying media are fed into the inside of the protective suit, and are also discharged from the inside of the suit via the at least one maintenance adapter with a detachable and sealing connection to the at least one aperture of the protective suit. This allows the protective suit to remain closed during the introduction and discharging of the cleaning and disinfecting fluid and/or the introduction and discharging of the drying gas. In particular, the one access opening for a person in the suit formed by the zipper of the suit is closed, which in contrast to the described prior art, since the media feed and discharge takes place via the at least one maintenance adapter with detachable and sealing connection that is connected to the least one aperture of the suit. Thus, the maintenance media can be fully distributed automatically in the suit such that the multifunctional racks, especially the lances to go in leg and arm opening are not needed anymore. This also eliminates the time-consuming mounting of the suit to such a multifunctional rack. With the tighter access to the inside of the closed (zipped up) protective suit via at least one maintenance adapter, a leak test of the suit on the at least one maintenance adapter is possible. A suitable valve control ensures the successive introduction of different media into the inside of the protective suit and to discharge them from the inside of the protective suit without loosening or changing the maintenance adapter or at least one of the hoses required to connect the maintenance adapter with the corresponding introduction system. All maintenance operations thus can be carried out with at least one maintenance adapter connected with one detachable and sealing connection to the at least one aperture of the protective suit and the discharge hose connected with the latter. As compared to conventional treatment systems, both the temporal and the physical effort for a serviceman is massively reduced.

In an embodiment, the control valve with a suitable sensor ensure that both temperature and internal pressure of the protective suit, respectively, remain in a predetermined range during the maintenance process.

In another embodiment, the protective suit can also be hung in the invention by the foot areas, so that the head part of the protective suit will be hanging down. In order to ensure circulation of the cleaning and disinfecting fluid and the drying gas or other maintenance media inside the suit, the cleaning and disinfecting fluid or the drying gas and possibly other maintenance media can be discharged through a discharge system at the at least one maintenance adapter. During the maintenance, condensation can form inside the protective suit, which can build up below the head area of the suit, for example, condensation from a cleaning fluid, a disinfectant solution, etc. This condensate, by arranging an additional suction device inside the head part of the suit, can be vacuumed or removed. The suction device may also be connected to the at least one maintenance adapter so that the extracted condensate is discharged through the at least one maintenance adapter.

The drying gas may be, in one embodiment, drying air, in particular warm air. For this purpose, a heating fan can be provided that generates a volume flow which is passed through the at least one maintenance adapter into and distributed automatically within the CPS. The term "fluid" includes for the purposes of the present application all flowable substances, regardless of their physical state. In particular, the term fluid includes gaseous or liquid substances or substances having both gaseous and liquid components, such as a vapor.

The system and method according to an embodiment the invention may contain an integrated water softening device for the water used in the maintenance. An integrated water treatment and reuse system for the water used for the maintenance can also be possible. The controller of the system according to the invention can automatically detect and record measured data generated in the course of maintenance so that the data clearly associated to the maintenance of the respective protective suit can be called and downloaded.

In one embodiment the process steps b (cleaning and disinfecting) and c (drying) can be carried out automatically by a control system and in particular fully automatically. The time and effort involved in manual maintenance is further reduced. A serviceman needs only to connect at least one maintenance adapter with at least one aperture or disconnect again at least one aperture after maintenance. All other maintenance steps until the examination and the valve inspection and the zipper treatment, can be performed automatically by the control device.

In a further embodiment, it can be provided that after step b) and before step c), a step b1) may be performed where a compressed gas for leak testing of the suit is directed through the at least one maintenance adapter into the inside of the suit until a predetermined pressure level is reached. The predetermined pressure level is then maintained for a predetermined period, after which time the gas is discharged through the at least one maintenance adapter in the protective suit. The pressurized gas may be for example, compressed air. In the process step b1), a warning message can also be issued if the pressure level falls under a defined limit within the predetermined period of time. The warning may include a logging. Accordingly, a leaky protective suit can be repaired and immediately reassessed. Also, the process step b1) can be carried out by the control device automatically, in particular fully automatically. Due to the tight connection of the at least one maintenance adapter to the at least one aperture of the suit, the pressure test, as already explained, can also be effected via the at least one maintenance adapter, via which also the cleaning and drying is carried out.

For the leak test of the suit, a stabilizing pressure can be set and maintained for a predetermined period by the control of the pressurized gas as was previously discussed. A higher test pressure can be set by appropriate adjustment of the supplied gas pressure and the suit can be closed by controlling the valve timing. For a predetermined period, the pressure measuring system measures in this closed state, a possible drop in pressure inside the suit. If this pressure drop exceeds a limit value, the suit does not meet the sealing requirements and a warning can be emitted. The test result can be automatically registered by the control device and documented for later review. A corresponding evaluation of the test results is done for the issuing of the warning message. The leak test system can also be integrated in the control device of the inventive system.

The at least one aperture of the suit may be at least one valve aperture, in particular at least one incoming air valve aperture and/or at least one exhaust valve aperture of the protective suit. Chemical Protection Suits count typically one or more exhaust valve apertures and partly one incoming air valve aperture, where the air inhaled by the user of the protective suit is directed via the incoming air valve aperture and the exhaled air is removed through the exhaust valve aperture(s). An exhaust valve aperture(s) are required so that the exhaled air does not produce a pressure in the suit.

As explained above, the present invention relates to particular Chemical Protection Suits of types 1a-ET and 1b-ET. Suits of type 1a-ET own a worn under the suit respirator and SCBA. Exhaust valve apertures are necessary and prescribed in this case. An incoming air valve aperture is optional, especially for breathing air or air conditioning. Where only one exhaust valve aperture is present, a test connection on the suit must be present. Suits of type 1b-ET have, worn over the suit, a respirator and a SCBA. Suits of type 1a ET must, according to DIN EN 943-1, be equipped with at least one exhaust valve as exhaust air device so that the CPS cannot be in overpressure. These exhaust valves are in most cases (except for the Typ1b-ET) in the neck or back of the head of the CPS. The same applies to the suits of type 1b-ET in the eventuality the respirator would be unable to pass consumed respiratory air directly into the open air. According to DIN EN 943-1 suits of type 1b-ET are equipped with an exhaust air system. They must be used for suits, for which air is directed from the respirator into the Chemical Protection Suit and, if the container device is worn outside of the suit, the air is directed from the pressure bottle for ventilation into the suit. With Chemical Protection Suits of type 1b ET, differences exist with respect to the types of masks employed. A distinction is made between two different versions: Version 1: a fully integrated in the suit mask; and Version 2: a separate mask which has no fixed connection to the CPS.

In a particularly simple manner, it is possible with the invention to connect at least one maintenance adapter, or, if needed, multiple maintenance adapters, even without removing the valve membranes contained in the incoming air and exhaust air valve apertures. It is also possible that the valve membranes are first removed and the at least one maintenance adapter is then connected to the incoming air/exhaust valve aperture.

The mere use of the provided apertures in the protective suit maintenance with the present invention leads to a further simplification. Alternatively, it is also conceivable that the at least one aperture is specifically provided for the purpose of maintenance as the maintenance aperture of the suit. Accordingly, a plurality of such maintenance apertures may be provided, which can, according to the invention, be connected to multiple maintenance adapters. It is also conceivable to have a visor or mask aperture for at least one aperture of the suit that, during use of the suit, is closed with an appropriate visor and mask. In this case, a sealing plate can be installed in the hole instead of the visor or mask, the latter having one or more suitable connecting apertures for one or more maintenance adapter.

According to another embodiment, the cleaning and disinfecting fluid can be a tempered cleaning and disinfecting vapor. The cleaning and disinfecting vapor is brought to a predetermined temperature level for cleaning by means of a tempering device, optionally in conjunction with a temperature sensor. In this embodiment, a steam cleaning method can be used instead of the conventional sputtering technique. The cleaning and disinfecting steam is distributed particularly evenly and for the purposes of thermal gravity automatically into the suit, even without using a multifunctional rack. In particular, the suit is inflated dimensionally stable by supplying the cleaning and disinfecting vapor and/or by supplying an additional pressure gas, such as compressed air, in an otherwise closed state. As mentioned, for this cleaning no threading of the suit to a multifunctional rack, in particular no introduction of cleaning devices, such as cleaning lances or the like, in the extremities of the suit is required. In the head area, a suction system may be provided for up-collecting condensate as was previously explained.

In an embodiment, the cleaning and disinfecting vapor may be water vapor. When using a correspondingly heated water vapor, additional chemical disinfectants for the disinfection of the inside of the suit may not be required. The cleaning and disinfecting steam can thus be formed by pure steam, which simultaneously ensures the required disinfection level in addition to the cleaning efficiency. The germs located in the inside that could return on the user of the suit will be killed by a sufficiently high temperature of the steam. This also allows the foregoing of the subsequently described rinsing process, which is normally required to remove a chemical disinfectant from the inside of the suit.

The homogeneous distribution of the cleaning and disinfecting vapor and the associated increase in the humidity inside the suit, causes a condensation of the cleaning and disinfecting steam at or on the inner material of the suit. The outflowing condensate is obtained by the cleansing effect of the inside of the suit. To remove the condensate liquid from the down hanging head part of the suit, the at least one maintenance adapter may also be connected to a suction hose, which via a clutch mechanism is connected inside of the head part of the suit to a suction device. Thus, the condensate can be sucked out of the protective suit.

As an alternative to the above-mentioned steam cleaning, a foam and disinfection cleaning is possible. In this embodiment, a cleaning and optionally disinfecting foam is used as a cleaning and disinfecting fluid and is introduced into the inside of the protective suit, distributed therein, and then completely discharged.

In particular, if the suit does not tolerate the necessary temperatures required to kill germs on the inside of the suit, a separate, for example, chemical disinfectant can be admixed to the cleaning and disinfecting fluid. Then, the inside of the suit is equipped with a flushing fluid, for example steam, rinsed to remove the disinfectant out of the protective suit after draining the cleaning and disinfecting fluid with the admixed disinfectant. The flushing fluid is thereby directed through the at least one maintenance adapter into the inside of the suit and removed from the protective suit. For the admixing of the disinfectant, a metering device may be provided with a dosing pump. The required amount of disinfectant is then fed to the hose for the cleaning and disinfecting fluid via a bypass.

According to another embodiment, the protective suit can be set specifically during the introduction and of discharging the cleaning and disinfecting fluid by introducing a pressurized gas under the dimensional stability of the suit guaranteeing expansion pressure. This can also take place during further process steps, in particular during rinsing and/or during drying. The pressurized gas can also be supplied and discharged via the at least one maintenance adapter. In this configuration, the suit is set for maintenance by using compressed gas, especially compressed air, at a value suitable for the suit expansion pressure. This ensures homogeneous distribution of maintenance media fed into the suit and allows them to reach all areas of the suit. The suit material expands to its full volume and in particular in the case of a steam cleaning the condensate is free to converge in the head part of the suit. The supply of the compressed gas may take place via a compressor via the same line as the feeding of the cleaning and disinfecting fluid, in particular a water vapor.

To ensure the required tightness for the pressure test, the protective suit is closed during the maintenance. This is especially true for the zipper forming the access opening of the suit for a person.

In a further embodiment, a first maintenance adapter with a first aperture of the protective suit may be connected in a detachable and sealed manner, and a second adapter with a second maintenance aperture of the suit may also be connected in a detachable and sealed manner. The introduction of the cleaning and disinfecting fluid is done via the first maintenance adapter and the discharge of the cleaning and disinfecting fluid is accomplished via the second maintenance adapter. The introduction of the drying gas is done via the first or second maintenance adapter and the discharge of the drying gas is accomplished via the second or first maintenance adapter.

The first and second apertures may be valve apertures of the protective suit, for example, incoming air/exhaust air valve apertures. However, they may also be other apertures. The introduction of the pressurized gas can be carried out via the first maintenance adapter or the second maintenance adapter and the discharge of the pressurized gas can be carried out via the second maintenance adapter or the first maintenance adapter. The supply of rinsing fluid to rinse the protective suit can take place via the first or the second maintenance adapter and the discharge of the rinsing fluid can take place via the second or the first maintenance adapter.

As already explained, the maintenance adapters according to the invention safely provide both a sealing and detachable connection between the external atmosphere and the atmosphere inside the suit. In the aforementioned embodiments, the feed and the drain of the respective media each take place through different maintenance adapters. However, it is also possible for some or all of the maintenance media to be fed and discharged via the same maintenance adapter. As already explained, an appropriate valve control is provided by the invention in order to sequentially switch between the supply and discharge of different media without having to disconnect the maintenance adapter or supply and discharge hose associated with the maintenance adapters. If a supply and discharge is carried out through the same maintenance adapter, hose-in-hose systems can be used.

According to another embodiment, the maintenance of the suit can be carried out in a closable maintenance cabin. The detachable and sealed connection of at least one maintenance adapter is carried out by the at least one aperture outside the maintenance cabin and the protective suit can also be automatically moved into the maintenance cabin. The process in the maintenance cabin can be in particular fully automatic. The maintained suit can also be returned from the maintenance cabin automatically via the control device in particular fully automatically. The maintenance cabin is especially splash proof Dripping water can escape. The tight connection of the at least one maintenance adapter with the at least one aperture before maintenance and the release of the at least one maintenance adapter from the at least one aperture after the maintenance can be performed manually by a serviceman outside the cabin. The maintenance cabin can be automatically or manually opened or closed before the start and at the end of maintenance (fully). In the closed maintenance cabin, automatically cleaning, disinfecting, and drying of the outside of the respective protective suit can be also done. The maintenance cabin also permits automatic black and white separation, i.e. a reliable separation between unpurified and purified protective suits. The access system to reach the protective suits in the maintenance cabin (and possibly for moving out of the cleaned suits from the maintenance unit) may comprise rails on which transport carriages are guided (this way, the protective suit(s) can be moved in and out of the maintenance cabin). Also conceivable is the use of telescopic rails on which the protective suits are suspended, for example, by their foot parts; the telescopic rails can then be retracted or driven to retract and displacing the protective suits in and out of the maintenance cabin. The control of the transport slide or of the telescopic rails is done automatically by access system according to the invention, for example controlled by the control device.

In a further embodiment, it can be provided that a plurality of protective suits can be maintained simultaneously with the invention's method or system. There are then correspondingly for each of the one or more protective suits, maintenance adapters according to the invention, each having one or more apertures, for example, valve ports as incoming and/or exhaust air valve aperture(s), connected to the protective suits. It is then possible to be provided with a common cleaning and disinfection fluid feeding system, a common drying gas feeding system, a common leak test system (each with a pressure measuring device per suit), a common metering device, a common flushing device and/or a common form stability pressure system for all protective suits. A common control device may be configured for the simultaneous maintenance of all the protective suits provided. However, it is also possible that some or all of the aforementioned devices are provided multiple times, in particular one time for a protective suit.

In another embodiment, the invention provides an automated cleaning, disinfecting, and drying combined with an automated (in conformity with DIN and manufacturer) leak test. Accordingly, the time and physical effort for an operator is significantly reduced. This applies in particular by waiving the need for a multifunctional rack for inside maintenance due to the inventive use of the maintenance adapters that are directly connected to possibly already existing apertures of the suit. By using steam cleaning, additional cleaning agent or disinfectant may, under certain conditions, also not be needed which also reduces water consumption.

Figure 1:
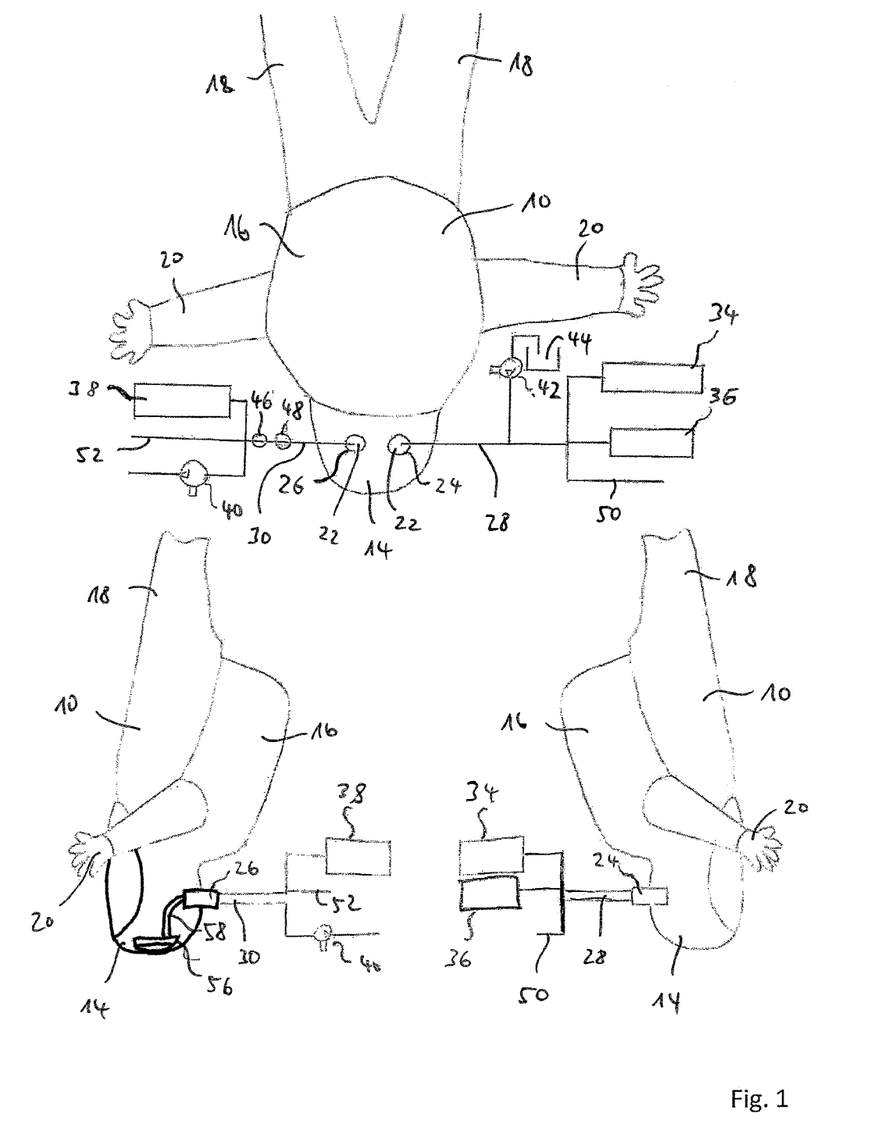
FIG. 1 shows a perspective view of a system for the maintenance of a Chemical Protection Suit.
Figure 2:
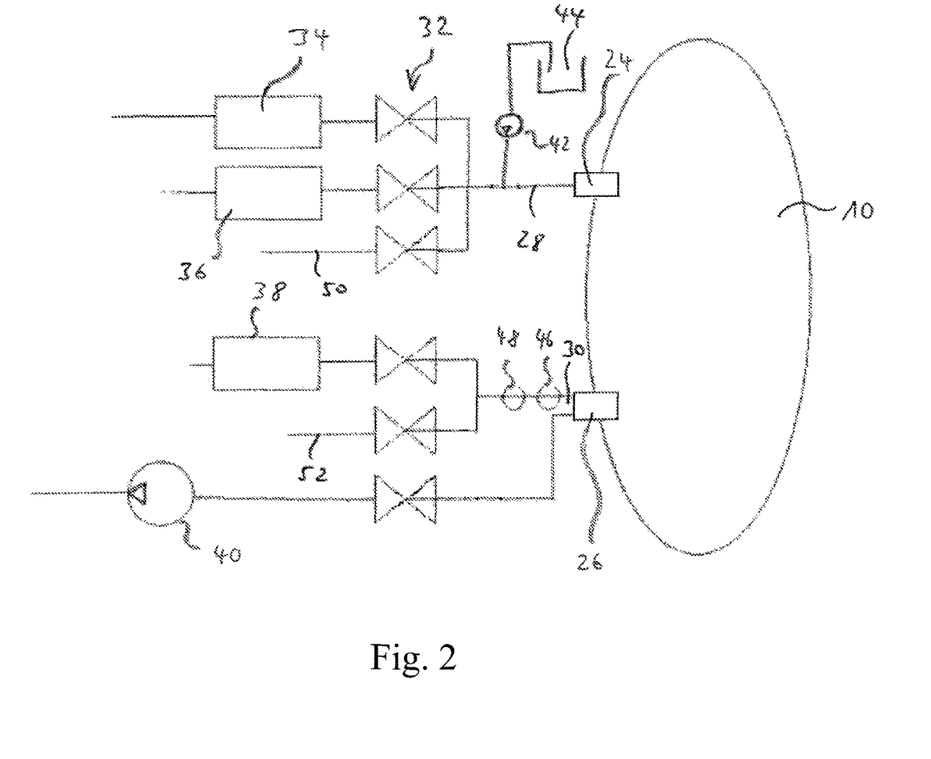
FIG. 2 shows a system for the maintenance of a Chemical Protection Suit.
Figure 3:
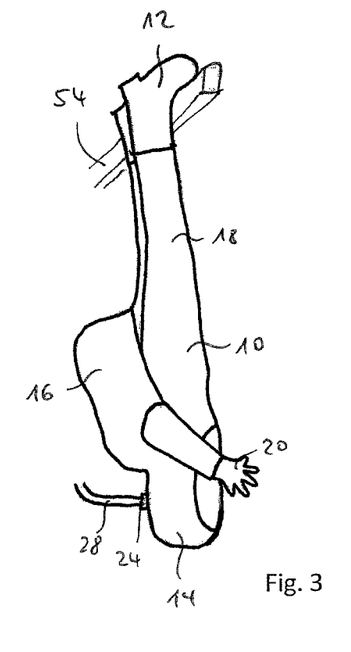
FIG. 3 shows a perspective view of a system for the maintenance of a Chemical Protection Suit.
Figure 4:
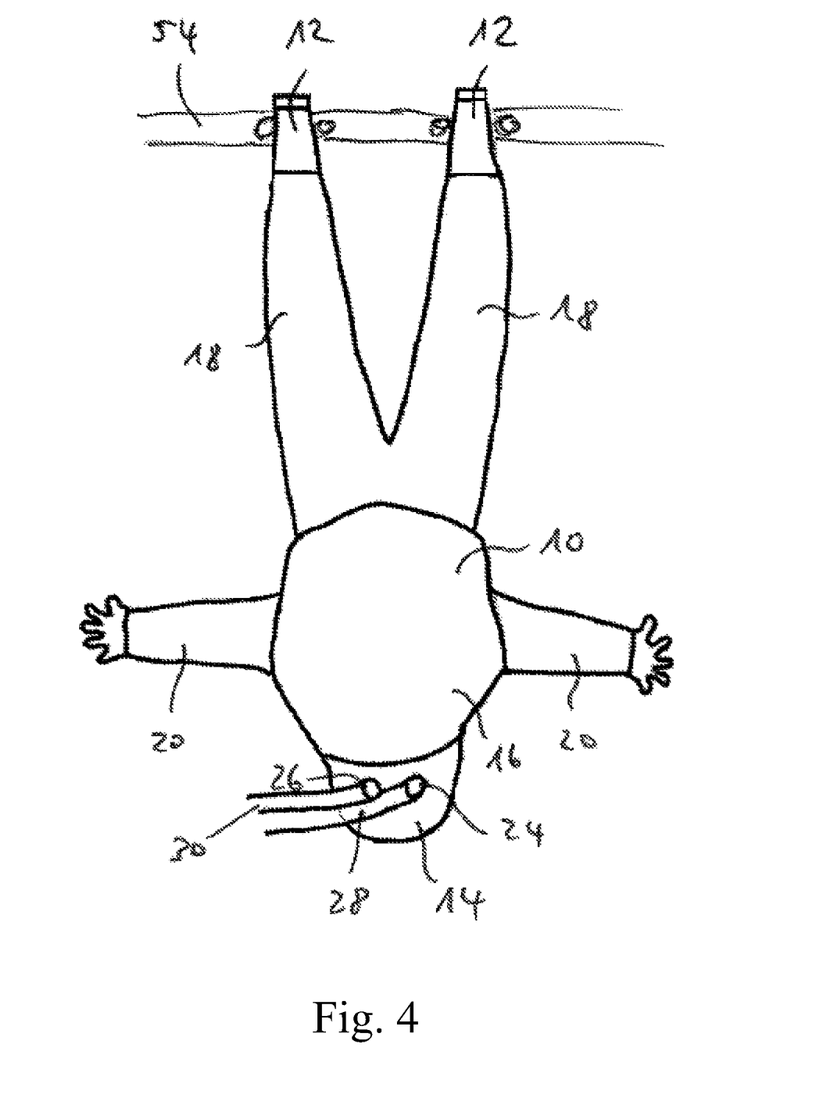
FIG. 4 shows a rear view of a system for the maintenance of a Chemical Protection Suit.

Unless otherwise stated, identical reference numerals refer to identical items. In the figures, a Chemical Protection Suit is generally referred to with the reference numeral 10, the Chemical Protection Suit is illustrated in FIG. 2 only by an ellipse. The Chemical Protection Suit is shown in FIGS. 1, and 3-4, as suspended from the foot parts 12 so that the head part 14 of the Chemical Protection Suit hangs down. The Chemical Protective Suit 10 further has a body part 16 and leg parts 18 and arm and hand parts 20. It is in the example a Chemical Protection Suit of type 1a or 1b ET-ET.

On the back of the head part 14, as shown in FIGS. 1-4, are the two exhaust air valve apertures 22, wherein in the example shown a first maintenance adapter 24 with a detachable and sealing connection is loosely connected with the first exhaust air valve aperture 22 and a second with a detachable and sealing connection maintenance adapter 26 with a second exhaust air valve aperture 22. A first hose 28 is connected to the first maintenance adapter 24 and a second hose 30 is connected to the second maintenance adapter 26. To be more explanatory of the maintenance adapter with the help of FIG. 2, valve control 32, maintenance adapters 24 and 26 may be connected to different media supply and media discharge. During the maintenance of Chemical Protection Suit 10 with the inventive system, the one-person entry zipper is tightly closed.

Still referring to FIGS. 1-2, the reference number 34 corresponds to a steam generator of a cleaning and disinfection fluid supply system. Number 36 refers to a compressed air compressor which belongs to a leak test system of the inventive system. Number 38 shows the heating fan of a dry gas supply system and number 40 a pump. Furthermore number 42 is a dosing pump which belongs to a metering device of the inventive system. The dosing pump 42 is connected to a dosing system 44 for disinfectant. By reference number 46, a pressure sensor and by reference number 48 a temperature sensor of the system according to the invention are shown in FIG. 2 the water vapor generator 34, the compressed air compressor 36, the heater fan 38, and the pump 40 are each connected via hoses 28 and 30 to a valve of the valve control device 32, respectively. In addition, a first discharge line 50 and a second discharge line 52 are provided, which are likewise in each case connected via a valve of the valve control device 32 to the first hose 28 and second hose 30. It should be noted that the control valve 32 is shown for illustrative purposes only in FIG. 2.

The operation of the system for maintenance of Chemical Protection Suit is further explained below. First, the Chemical Protection Suit 10 is prepared for maintenance, where the ventilation unit, attachments, an anti-fog visor, back cushion, membranes (discs) of the exhaust air device (exhaust valves) and covers of the suit valves are all or individually removed and a visual inspection of the Chemical Protection Suit 10 is performed to notice obvious damage. The Chemical Protection Suit 10 is subsequently or previously arranged upside down with or without the described attachments to the foot part 12 at the maintenance system, presently on a schematically shown rail in FIGS. 3 and 4 at the reference number 54. On the rail number 54, there may be a telescopic slide with which the Chemical Protection Suit 10 can be operated automatically or manually in and out of a non-illustrated maintenance cabin of the maintenance system. The maintenance cabin can be closed automatically or manually before maintenance and be opened automatically or manually after the maintenance. For the control of the inventive system, including a possibly provided telescopic rail 54, a control device (not illustrated here) is provided.

After suspending the Chemical Protection Suit on rail 54, the first maintenance adapter 24, for example, is connected manually with a detachable and sealing connection by a serviceman to the first exhaust air valve aperture 22 (FIG. 1) and the second maintenance adapter 26 is connected via a manually detachable and sealing connection to the second exhaust air valve aperture 22. In addition, a suction device 56 is provided to suction the condensate accumulated in the area of head part 14 in the context of the maintenance. The head part is connected via a suction line 58 with the second maintenance adapter 26. To connect the maintenance adapters 24, 26 and to arrange the suction device 56 including suction line 58 in the Chemical Protection Suit 10, the zipper (not shown) forming an access to the Chemical Protection Suit 10 is open. This zipper is closed after installation of the components mentioned. Subsequently, the Chemical Protection Suit 10 as explained, for example, can be moved into a maintenance cabin of the system.

Now the maintenance process starts. First, the Chemical Protection Suit 10 is connected via an aperture to the valve associated with the compressed air compressor 36 using the compressed air compressor 36 under an expansion or dimensional stability pressure. In that regard, the compressed air compressor 36 is also part of a dimensional stability pressure device according to the invention. The dimensional stability pressure is sufficient so that the Chemical Protection Suit 10 can expand to its full or nearly full volume. Subsequently, the steam generator 34 associated valve is opened and through the steam generator 34 water vapor is introduced as a cleaning and disinfecting fluid through the first maintenance adapter 24 at a preset temperature inside the Chemical Protection Suit 10 where it is automatically distributed evenly among others due to the dimensional stability pressure. The control device controlled thereby via the pressure sensor 46 and the temperature sensor 48 temperature and pressure inside the Chemical Protection Suit 10 and adjusts them if necessary after the attainment of a respective set point. As long as the water vapor can maintain a sufficient temperature for killing germs in the suit, the supply of a separate disinfectant is not required. Otherwise, for example, a chemical disinfectant can be mixed with the water vapor via the dosing pump 42 from the dosing system 44. The water vapor condenses on the inner surfaces of the Chemical Protection Suit 10 and the draining condensate collects in the head part (of the suit) 14, where it is sucked by the suction device 56 via the suction hose 58 and in particular discharged via pump 40. Provided that the water vapor disinfectant has been added, a rinsing is done with pure water vapor in the inside of the protective suit right after and chemicals are pumped through the pump 40.

After the cleaning process, the leak test is performed. For that purpose, the Chemical Protection Suit 10 is pressurized by the compressed air compressor 36 first under a stabilizing pressure and the pressure stabilization is maintained during a predetermined time interval. Subsequently, the Chemical Protection Suit 10 is pressurized by the compressed air compressor 36 at the higher test pressure and the line system is closed by closing the valves. The pressure sensor 46 (FIGS. 1-2) monitors the pressure drop for a predetermined time period. The measurement results can be documented and recorded, for example by the control device. If the pressure drop above a limit value remains, the leak test, by aperture example, of the discharge line 52 associated valve is stopped so that the pressure in the Chemical Protection Suit 10 drops, for example, the dimensional stability pressure. In contrast, if under the leak test system an impermissibly high pressure drop is registered, the control device can output a warning signal and this measurement result may also be recorded. In this case, the Chemical Protection Suit 10 is unable be further used or repaired and must be re-examined prior to use.

Next, the drying process may begin, however it is also possible that the drying process is carried out prior to the leak test. Warm air is circulated by the heater fan 38 through the aperture associated with this valve inside the Chemical Protection Suit 10. The warm air absorbs the residual moisture in the Chemical Protection Suit 10 and dissipates it over a return valve aperture of the first maintenance adapter 24 and via the discharge line 50. After a predetermined period, the drying process is terminated.

When using a maintenance cabin, an outer cleaning, disinfection and drying can also take place, particularly before or after the above-mentioned maintenance process. The Chemical Protection Suit 10 is then moved out of the cabin, in turn, for example, automatically controlled by the control device. Now the zipper of the Chemical Protection Suit 10 can be open by a serviceman and the serviceman can remove the drain device 56 and the suction line 58 from the inside of the head part 14 and release the maintenance adapters 24 and 26 of the exhaust air valve aperture 22. The Chemical Protection Suit 10 can now be removed for further use.

The invention claimed is:

1. A method for maintaining at least one protective suit, the method comprising:
    a) connecting at least one maintenance adapter in a detachable and sealing manner to at least one valve aperture of the protective suit, the at least one maintenance adapter being separate from the at least one valve aperture of the protective suit;
    b) introducing compressed air into an inside of the protective suit to expand and stabilize the protective suit;
    c) introducing cleaning and disinfecting fluid into the inside of the protective suit through the at least one maintenance adapter while the protective suit is closed;

d) discharging the cleaning and disinfecting fluid from the protective suit through the at least one maintenance adapter;
e) passing a drying gas into the inside of the protective suit through the at least one maintenance adapter;
f) discharging the drying gas from the protective suit through the at least one maintenance adapter, wherein a valve control is configured to sequentially switch the introduction and the discharge of the cleaning and disinfecting fluid and the passing and discharge of the drying gas through the at least one maintenance adapter;
g) performing a leak test; and
h) disconnecting the at least one maintenance adapter from the at least one valve aperture.

2. The method according to claim 1, wherein the valve control comprises a pressure sensor, and wherein the leak testing comprises:
passing a pressurized gas through the at least one maintenance adapter into the inside of the protective suit until the protective suit reaches a predetermined pressure level;
stopping the passing of the pressurized gas when the predetermined pressure level is reached;
monitoring a pressure drop for a predetermined period of time using the pressure sensor; and
discharging the pressurized gas from the protective suit through the at least one maintenance adapter after expiration of the predetermined period of time.

3. The method according to claim 2, wherein a warning message is issued when the pressure sensor indicates that the pressure drops below a predefined threshold value during the predetermined period of time.

4. The method according to claim 2, wherein a control device is in communication with the valve control and is programmed to regulate the passing and discharge of the pressurized gas and is further programmed to measure a prevailing pressure for the predetermined period of time.

5. The method according to claim 1, wherein the protective suit is set during the introduction and discharging of the cleaning and disinfecting fluid by introducing a pressurized gas below a dimensional stability of the protective suit guaranteeing expansion pressure.

6. The method according to claim 2, wherein a first maintenance adapter is connected to a first valve aperture of the protective suit by a detachable and sealing connection and a second maintenance adapter is connected to a second valve aperture of the protective suit by a detachable and sealing connection, wherein the introduction of the cleaning and disinfecting fluid takes place through the first maintenance adapter and the discharge of the cleaning and disinfecting fluid through the second maintenance adapter, and wherein the introduction of the drying gas takes place through one of the first maintenance adapter and the second maintenance adapter and the discharge of the drying gas through whichever maintenance adapter does not introduce the drying gas.

7. The method according to claim 6, wherein the introducing of the pressurized gas takes places via one of the first and second maintenance adapter and the discharge of the pressurized gas takes place via whichever maintenance adapter does not introduce the pressurized gas.

8. The method according to claim 1, wherein the introduction and discharge of the cleaning and disinfecting solutions and the introduction and discharge of the drying gas takes place within a closable maintenance cabin.

9. A system for maintaining a protective suit, the system comprising:
at least one maintenance adapter coupled to at least one valve aperture of the protective suit by a detachable and sealing connection;
a compressed air supply connected to the at least one maintenance adapter for introducing compressed air into an inside of the protective suit to expand and stabilize the protective suit and to perform leak testing;
a cleaning and disinfecting fluid supply connected to the at least one maintenance adapter for introducing a cleaning and disinfecting fluid into an inside of the protective suit and for discharging cleaning and disinfection fluid from the protective suit when the suit is in a closed position;
a drying gas supply is connected to the at least one maintenance adapter for introducing a drying gas into the inside of the protective suit to dry the protective suit and for discharging the drying gas from of the protective suit; and
a control device programmed to sequentially switch the supply and the discharge of the cleaning and disinfecting fluid and the supply and discharge of the drying gas through the at least one maintenance adapter.

10. The system according to claim 9, further comprising a supply of pressurized gas and a pressure sensor wherein the pressurized gas is pumped from the supply into the protective suit through the at least one valve aperture via the at least one maintenance adapter until the pressure sensor detects that a predetermined pressure level is reached in the protective suit, wherein a prevailing pressure level in the protective suit is determined over a predetermined time period and the pressurized gas is discharged through the at least one maintenance adapter after the predetermined time period.

11. The system according to claim 10, further configured to output a warning message if the pressure sensor registers a pressure drop below a predefined threshold value within the predetermined time period.

12. The system according to claim 10, wherein the control device is programmed to control the sequential pumping and discharging of the pressurized gas into the protective suit and is further programmed to determine the prevailing pressure level in the protective suit over the predetermined time.

13. The system according to claim 9, further comprising a dimensional stability pressure system configured to introduce a pressurized gas through the at least one maintenance adapter, the pressurized gas set below a guaranteed expansion pressure of a dimensional stability of the protective suit during the introduction and discharge of cleaning and disinfecting fluid.

14. The system according to claim 9, further comprising:
a first maintenance adapter with a detachable and sealing connection with a first valve aperture of the protective suit;
a second maintenance adapter with a second valve aperture of the suit with a detachable and sealing connection;
wherein the cleaning and disinfecting liquid supply system is connectable with one of the first maintenance adapter and the second maintenance adapter such that introduction of the cleaning and disinfecting fluid through the first maintenance adapter and the discharge of the cleaning and disinfecting fluid through the second maintenance adapter takes place; and wherein the drying gas supply is connectable with one of the first maintenance adapter and the second maintenance adapter such that the introduction of the drying gas occurs through one of the first maintenance adapter and the second maintenance adapter and the discharge of the drying gas occurs through whichever maintenance adapter does not introduce the drying gas.

15. The system according to claim 14, wherein a supply of pressurized gas is connected to one of the first maintenance adapter and the second maintenance adapter such that the introduction of the pressurized gas occurs through one of the first maintenance adapter and the second maintenance adapter and the discharging of the pressurized gas occurs through whichever one of the first maintenance adapter and the second maintenance adapter is not used for the introduction of pressurized gas.

16. The system according to claim 9, further comprising a closable maintenance cabin to carry out the maintenance of the protective suit, the closable maintenance cabin including one or more transport carriages configured to move the protective suit into and out of the closable maintenance cabin.

\* \* \* \* \*